(12) United States Patent
Bailey et al.

(10) Patent No.: US 8,810,236 B2
(45) Date of Patent: Aug. 19, 2014

(54) APPARATUS AND ASSOCIATED METHODS

(75) Inventors: Marc J A Bailey, Cambridge (GB); Elisabetta Spigone, Cambridge (GB)

(73) Assignee: Nokia Corporation, Espoo (FI)

( * ) Notice: Subject to any disclaimer, the term of this patent is extended or adjusted under 35 U.S.C. 154(b) by 1195 days.

(21) Appl. No.: 12/720,604

(22) Filed: Mar. 9, 2010

(65) Prior Publication Data

US 2011/0221425 A1   Sep. 15, 2011

(51) Int. Cl.
| | | |
|---|---|---|
| *G01R 11/04* | (2006.01) | |
| *G01N 33/543* | (2006.01) | |
| *C12Q 1/00* | (2006.01) | |

(52) U.S. Cl.
CPC ............ *C12Q 1/002* (2013.01); *G01N 33/5438* (2013.01)
USPC ...... 324/157; 324/755.09; 324/692; 324/693; 324/724; 324/128

(58) Field of Classification Search
USPC ............. 324/157, 755.09, 692, 693, 724, 128
See application file for complete search history.

(56) References Cited

U.S. PATENT DOCUMENTS

| | | | |
|---|---|---|---|
| 4,824,529 A | 4/1989 | Thompson et al. ................ 204/1 |
| 4,832,797 A * | 5/1989 | Vadgama et al. ............. 205/778 |
| 2003/0049865 A1* | 3/2003 | Santini et al. .................. 436/518 |
| 2003/0104590 A1* | 6/2003 | Santini et al. .................. 435/174 |
| 2003/0134433 A1 | 7/2003 | Gabriel et al. ................ 436/518 |
| 2004/0058446 A1* | 3/2004 | Wolff et al. .................... 435/455 |
| 2004/0259073 A1* | 12/2004 | Hassibi et al. ..................... 435/4 |
| 2005/0191620 A1 | 9/2005 | McDevitt et al. ................. 435/5 |
| 2007/0299385 A1* | 12/2007 | Santini et al. .................... 604/19 |
| 2008/0084205 A1* | 4/2008 | Zimmer ......................... 324/252 |
| 2008/0138877 A1* | 6/2008 | Dzekunov et al. .......... 435/173.6 |
| 2008/0215931 A1 | 9/2008 | Boss et al. ....................... 714/57 |
| 2009/0233330 A1* | 9/2009 | Sachs et al. ...................... 435/39 |

FOREIGN PATENT DOCUMENTS

| | | | |
|---|---|---|---|
| CN | 101568828 A | | 10/2009 |
| CN | 101581685 A | | 11/2009 |
| GB | 2204408 A | * | 11/1988 |
| WO | WO-01/59453 A2 | | 8/2001 |
| WO | WO 2008/102120 A1 | | 8/2008 |
| WO | WO 2008/102120 A1 | | 8/2008 |
| WO | WO 2010/078569 A2 | | 7/2010 |

OTHER PUBLICATIONS

Clark et al. (Annals of the New York Academy of Sciences, vol. (102), issue 1, Article first published online: Dec. 15, 2006).*
U.S. Appl. No. 61/099,370, filed Sep. 2008, Chan et al.*

(Continued)

*Primary Examiner* — Huy Q Phan
*Assistant Examiner* — Temilade S Rhodes-Vivour
(74) *Attorney, Agent, or Firm* — Harrington & Smith

(57) ABSTRACT

An analyte sensor apparatus and a corresponding fluid medium,
the analyte sensor apparatus comprising a sensing element, the external surface of which comprises a membrane to inhibit exposure of the sensing element;
the corresponding fluid medium comprising a receptor species and an activatable species, the receptor species for interacting with an analyte to activate the activatable species, activation of the activated species causing increased porosity of the membrane of an in-contact analyte sensor apparatus to correspondingly increase exposure of the sensing element to allow for production of a detectable electrical signal which can be used to sense the presence of the analyte.

18 Claims, 6 Drawing Sheets

(56) References Cited

OTHER PUBLICATIONS

Figure 1:
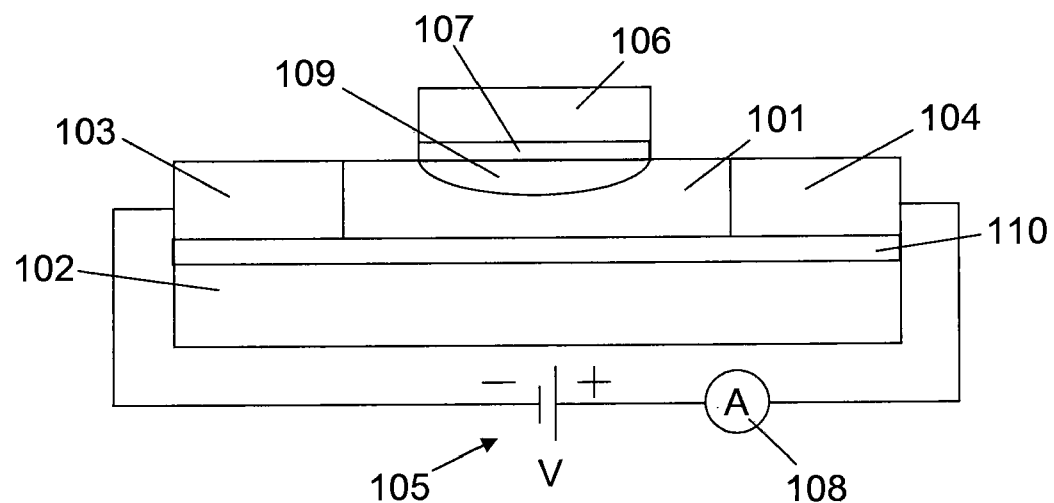

Martinez, et al., "Highly Efficient Biocompatible Single Silicon Nanowire Electrodes with Functional Biological Pore Channels", Nano Letters, vol. 9, No. 3, (2009), pp. 1121-1126.

Bayley, et al., "Stochastic Sensors Inspired by Biology", Macmillan Magazines Ltd., vol. 413, No. 6852, (2001), pp. 226-230.

Majd, et al., "Applications of Biological Pores in Nanomedicine, Sensing, and Nanoelectronics", vol. 21, No. 4, (2010), pp. 439-479.

Misra, N. et al.; "Bioelectronic silicon nanowire devices using functional membrane proteins"; Proceedings of the National Academy of Sciences, vol. 106, No. 33; Aug. 18, 2009; pp. 13780-13784; National Academy of Sciences; XP007915888.

Panchal, R. et al.; "Pore-Forming Proteins and their Application in Biotechnology"; Current Pharmaceutical Biotechnology, vol. 3, No. 2; Jan. 1, 2002; pp. 99-115; Bentham Science Publishers, NL; XP009122720.

Braha, O. et al.; "Designed protein pores as components for biosensors"; Chemistry and Biology, vol. 4, No. 7; Jan. 1, 1997; pp. 497-505; Current Biology, London, GB; XP009006124.

\* cited by examiner

APPARATUS AND ASSOCIATED METHODS

TECHNICAL FIELD

The present disclosure relates to the field of nanowire sensors, associated methods and apparatus, and in particular concerns an indirect sensing mechanism that couples analyte-receptor recognition to an increase in porosity of a membrane layer. The disclosure also relates to the recycling of an analyte sensor apparatus. One or more techniques described herein may or may not be suitable for the detection of particular sets of molecules in gases or aqueous fluids, or for health monitoring using portable electronic devices.

BACKGROUND

The detection of biological and chemical species is central to many areas of healthcare and the life sciences, ranging from uncovering and diagnosing disease to the discovery and screening of new drugs. The development of advanced devices that enable reliable and sensitive detection of these species is therefore important.

Central to detection is the signal transduction associated with selective recognition of a biological or chemical species of interest. Planar semiconductors can serve as the basis for chemical and biological sensors in which detection can be monitored electrically and/or optically. For example, a planar field effect transistor (FET) can be configured as a sensor by modifying the gate oxide (without gate electrode) with molecular receptors or a selective membrane for the analyte of interest. Binding of a charged species then results in depletion or accumulation of carriers within the transistor structure. An attractive feature of such chemically sensitive FETs is that binding can be monitored by a direct change in conductance or related electrical property, although the specificity for different biological molecules is limited.

The physical properties limiting sensor devices fabricated in planar semiconductors can be readily overcome by exploiting nanoscale FETs. In this regard, nanoscale sensors based on nanowires and nanotubes have received considerable recent attention. Nanowires and nanotubes have the potential for very high sensitivity (single-molecule detection in some cases) since the depletion or accumulation of charge carriers, which are caused by binding of a charged molecule at the surface of the nanowire/nanotube, can affect the entire cross-sectional conductional pathway of these nanostructures. Furthermore, the small size of the nanowires and nanotubes combined with recent advances in assembly suggest that dense arrays of sensors could be prepared.

Research in this area has shown that nanowire FET devices can be functionalised with immobilised probe molecules such as surface receptors for the detection of specific molecular species in solution. The first published example demonstrating the ability of a nanowire FET to detect species in solution dates back to 2001, where a p-type Si nanowire device was used as a pH sensor by chemical modification of the silicon oxide surface [Y. Cui et al, Science, 293, 1289 (2001)]. This silicon nanotube-based device was subsequently modified to enable it to detect the presence of various proteins.

Using the same principle, such sensors have been used as tools for drug discovery, where the binding or inhibition of binding is solved as an increase or decrease in conductance, respectively [W. U. Wang et al, PNAS, 102, no. 9, 3208 (2005)]. In addition, single-stranded DNA fragments have been detected as an increasing conductance using a nanowire surface modified with peptide nucleic acid (PNA) receptors [J. Hahm et al, Nano Letters, 4, no. 1, 51 (2004)].

Further research has demonstrated the detection of a virus using an antibody receptor [F. Patolsky et al, PNAS, 101, no. 39, 14017 (2004)], wherein the binding and the release of the virus particles caused changes in the conductance of the nanowire device.

Whilst nanowire-based sensors offer a number of key benefits with respect to other technologies (direct, label-free, real-time detection, ultrahigh sensitivity, high selectivity, potential for integration into arrays on a massive scale), the above-mentioned devices also have their drawbacks. Reports of the use of FETs to directly sense the presence of biological molecules have shown inconsistent results, partly due to the complexity of the charged species being measured. In addition, such devices cannot be reused after the sensing event and must therefore be disposed of. Furthermore, the correct attachment of the receptor molecules to ensure highly specific binding requires sometimes complicated surface functionalisation.

Development of surface chemistry to couple biological molecules to a surface is a common problem in the development of sensors, and numerous solutions exist. One solution exploits the capacity of certain types of lipid molecules to form membranes, for example the plasma membrane that encloses the cytoplasm of many types of biological cells. Some types of receptor molecules have evolved to bind their analyte when they are embedded in lipid membranes, and this specific receptor-analyte recognition leads to an alteration of some electrochemical property of the membrane, such as transmembrane conductance or capacitance.

Recent work has suggested that lipid membranes can serve as functional interfaces between the biological analyte and the nanoelectronic sensor [N. Misra et al, PNAS, 106, no. 33, 13780 (2009)]. In this study, Si nanowires were covered by a continuous lipid bilayer membrane that formed a shield between the nanowire and the species in solution. The incorporation of transmembrane peptide pores enabled ionic species to transport across the membrane and generate an ionic-electronic signal. This work suggests that lipid membrane-coated nanowire devices incorporating functional membrane proteins could serve as versatile platforms for developing biosensors that are based on the functionality of the transmembrane protein pores.

The listing or discussion of a prior-published document or any background in this specification should not necessarily be taken as an acknowledgement that the document or background is part of the state of the art or is common general knowledge. One or more aspects/embodiments of the present disclosure may or may not address one or more of the background issues.

SUMMARY

According to a first aspect, there is provided an analyte sensor apparatus and a corresponding fluid medium,
 the analyte sensor apparatus comprising a sensing element, the external surface of which comprises a membrane to inhibit exposure of the sensing element;
 the corresponding fluid medium comprising a receptor species and an activatable species, the receptor species for interacting with an analyte to activate the activatable species, activation of the activated species causing increased porosity of the membrane of an in-contact analyte sensor apparatus to correspondingly increase exposure of the sensing element to allow for production of a detectable electrical signal which can be used to sense the presence of the analyte.

The dimensions of the sensing element may vary from the macroscale (e.g. cm or mm) to the microscale (e.g. μm) or nanoscale (e.g. nm). The sensing element may comprise one or more nanowires or a planar structure. The sensing element may be coated by the membrane. The membrane itself may comprise any material which, until pores have been created in the membrane, is capable of inhibiting exposure of the sensing element to the fluid medium. The membrane may comprise a lipid or other molecules that form a barrier to certain species whose proximity to a nanowire may or may not change its conductance. In particular, the membrane may comprise a lipid, a phospholipid or mixtures of the two. The lipid may be dioleoyl phosphatidylcholine (DOPC). The DOPC may be doped with a fluorescent lipid probe such as NBD-PE (1,2-dioleoyl-sn-glycero-3-phosphoethanolamine-N-(7-nitro-2-1,3-benzoxadiazol-4-yl)).

The term "interacting" may imply that the receptor species and analyte interact with one another directly or indirectly. Furthermore, the term "interacting" may imply that the receptor species and analyte bind to one another.

There is provided a sensor that couples the specific interaction of an analyte and receptor to an increase in porosity of a membrane layer to indirectly detect the presence of an analyte. The term nanowire has been used to encompass nanotubes and such like.

The analyte sensor apparatus may be configured such that the analyte itself in-contact with the membrane does not cause increased porosity of the membrane. The receptor species may be capable of specifically interacting with the analyte. The receptor species may be an antibody, such as a mammalian antibody, but could be another affinity agent capable of specifically interacting with the analyte. The antibody may comprise immunoglobulin molecules, such as IgG molecules. The antibody may be a monoclonal antibody or a polyclonal antibody. Two or more monoclonal antibodies may be configured to interact with the same antigen. The analyte sensor apparatus may be configured such that the receptor species is bound to the membrane, but need not be. Likewise, the analyte sensor apparatus may be configured such that the receptor species is embedded in the membrane, but need not be. Binding or embedding of the receptor species may improve exposure of the binding sites to the analyte and increase the chances of forming an analyte-receptor complex.

The analyte may be a biological or chemical species of sufficient size and structure that the affinity reagent (herein described as an antibody) can recognise and bind with sufficient specificity and avidity. The analyte species may be an antigen. The analyte may be a pathogen. The analyte may be a viral, bacterial, fungal, eukaryotic or prionic pathogen.

The activatable species may be any species capable of creating pores in the membrane when activated by a specific analyte-receptor interaction event. The activatable species may comprise one or more complement proteins and may be configured such that activation of the activatable species by the analyte triggers a complement cascade to produce a membrane-attack complex from the complement proteins. The activatable species may be the C1 complement protein working in conjunction with other complement proteins. The term "activatable species" may refer to the group of complement proteins. The membrane-attack complex may cause increased porosity of the membrane. The membrane-attack complex may embed itself in the membrane. Embedding of the membrane-attack complex in the membrane may cause increased porosity of the membrane.

The fluid medium may or may not comprise a charged species configured to provide an ionic gradient across the membrane. The fluid medium may use a mixture of ions, pH and chemicals to ensure activation of the activatable species by the analyte. The fluid medium may or may not comprise a charged species configured to produce a detectable electrical signal when in-contact with the sensing element. The charged species may be a charged atomic species (such as a hydrogen ion) or a charged molecular species. The charged species may be a charged subatomic particle such as a proton or electron. The membrane may be configured to be impervious to these charged species. Increased porosity of the membrane caused by activation of the activatable species may allow the charged species to diffuse through the created pores in the membrane from the corresponding fluid medium to cause a change in charge concentration at the exposed surface of the sensing element. Where the charged species comprises protons, diffusion of the protons through the membrane from the corresponding fluid medium may cause a change in pH at the external surface of the sensing element.

The analyte sensor apparatus may comprise source and drain electrodes. The source and drain electrodes may be electrically connected to the sensing element such that an electrical current may flow from the source electrode through the sensing element to the drain electrode when a potential difference is applied across the source and drain electrodes. The analyte sensor apparatus may be configured such that electrical connectors are electrically connected to the source and drain electrodes to apply the potential difference. The analyte sensor apparatus may be configured such that the electrical connectors are removably connected to the source and drain electrodes. The analyte sensor apparatus may be configured such that the source and drain electrodes are electrically insulated from the corresponding fluid medium. The analyte sensor apparatus may be configured such that the conductance or other electrical property of the sensing element varies with charge concentration at the external surface of the sensing element.

The sensing element may be formed from an intrinsic or doped semiconducting material. The semiconducting material may be a p-type or n-type semiconducting material. The sensing element may be a silicon sensing element.

The analyte sensor apparatus may form part of a field-effect transistor. The field-effect transistor may be a nanowire field-effect transistor. The nanowire may be a hollow/solid tube. The analyte sensor apparatus may comprise a plurality of nanowires on a substrate. The analyte sensor apparatus may comprise one or more arrays of nanowires on a substrate. Advantageously, the respective arrays may be configured to be spaced apart from one another on the substrate such that the sensor is able to perform multiplexed sensing experiments. The analyte sensor apparatus may be integrated within a microfluidic system. The analyte sensor apparatus and fluid medium may be a kit. The kit may comprise a control amount of analyte.

According to a further aspect, there is provided a fluid medium (e.g. isolated fluid medium, which may mean isolated from a living or dead human/animal/plant/bacterial body) for use with a corresponding analyte sensor apparatus comprising a sensing element, the external surface of which comprises a membrane to inhibit exposure of the sensing element;

the fluid medium comprising a receptor species and an activatable species, the receptor species for interacting with an analyte to activate the activatable species, activation of the activated species causing increased porosity of the membrane of an in-contact analyte sensor apparatus to correspondingly increase exposure of the sensing element to allow for production of a detectable electrical signal which can be used to sense the presence of the analyte.

The analyte may be isolated from the fluid medium. The fluid medium may comprise control amounts of the analyte. The fluid medium may comprise charged species.

According to a further aspect, there is provided a method of sensing an analyte, the method comprising:

using/providing an analyte sensor apparatus and a corresponding fluid medium, the analyte sensor apparatus comprising a sensing element, the external surface of which comprises a membrane to inhibit exposure of the sensing element, the corresponding fluid medium comprising a receptor species and an activatable species, the receptor species for interacting with an analyte to activate the activatable species, activation of the activated species causing increased porosity of the membrane of an in-contact analyte sensor apparatus to correspondingly increase exposure of the sensing element to allow for production of a detectable electrical signal which can be used to sense the presence of the analyte; and exposing the analyte to the corresponding fluid medium and analyte sensor apparatus to allow for production of a detectable electrical signal which can be used to sense the presence of the analyte.

According to a further aspect, there is provided a computer program for sensing the presence of an analyte, the computer program comprising computer code to detect an electrical signal produced from an analyte sensor apparatus and a corresponding fluid medium, the analyte sensor apparatus comprising a sensing element, the external surface of which comprises a membrane to inhibit exposure of the sensing element, the corresponding fluid medium comprising a receptor species and an activatable species, the receptor species for interacting with an analyte to activate the activatable species, activation of the activated species causing increased porosity of the membrane of an in-contact analyte sensor apparatus to correspondingly increase exposure of the sensing element to allow for production of a detectable electrical signal which can be used to sense the presence of the analyte.

According to a further aspect, there is provided a method of recycling an analyte sensor apparatus, the method comprising:

providing an analyte sensor apparatus, the analyte sensor apparatus comprising a sensing element, the external surface of which comprises a membrane;

introducing a surfactant solution to interact with and break down the integrity of the membrane;

washing the external surface of the sensing element; and forming a new membrane on the external surface of the sensing element.

The surfactant may be introduced at a concentration greater than or equal to the critical micellar concentration of the lipid species. On the other hand, the surfactant may be introduced at a concentration lower than the critical micellar concentration. The surfactant solution may interact with and break down the integrity of the membrane until complete disruption of the membrane has occurred. The surfactant may be LDAO (Lauryldimethylamine-oxide). The sensing element may comprise one or more sensing elements.

According to a further aspect, there is provided the use of an analyte sensor apparatus and corresponding fluid medium for detecting the presence of an analyte, the use comprising:

providing an apparatus and corresponding fluid medium, the analyte sensor apparatus comprising a sensing element, the external surface of which comprises a membrane to inhibit exposure of the sensing element, the corresponding fluid medium comprising a receptor species and an activatable species, the receptor species for interacting with an analyte to activate the activatable species, activation of the activated species causing increased porosity of the membrane of an in-contact analyte sensor apparatus to correspondingly increase exposure of the sensing element to allow for production of a detectable electrical signal which can be used to sense the presence of the analyte; and instructing exposure of the analyte to the corresponding fluid medium and analyte sensor apparatus to allow for production of a detectable electrical signal which can be used to sense the presence of the analyte.

The present disclosure includes one or more corresponding aspects, embodiments or features in isolation or in various combinations whether or not specifically stated (including claimed) in that combination or in isolation. Corresponding means for performing one or more of the discussed functions are also within the present disclosure.

The above summary is intended to be merely exemplary and non-limiting.

BRIEF DESCRIPTION OF THE FIGURES

A description is now given, by way of example only, with reference to the accompanying drawings, in which:—

FIG. 1 illustrates schematically a planar field effect transistor;

FIG. 2 illustrates schematically a nanowire field effect transistor;

FIG. 3 illustrates schematically a typical conductance versus time plot for a nanowire sensor;

FIG. 4 illustrates schematically a phospholipid molecule, a lipid bilayer, a lipid micelle and a liposome;

FIG. 5 illustrates schematically a cross-section of a nanowire coated with a lipid bilayer;

FIG. 6 illustrates schematically the classical complement pathway;

FIG. 7 illustrates schematically the formation and subsequent exposure of a lipid bilayer coating on the surface of a nanowire;

FIG. 8 illustrates schematically a device comprising the apparatus described herein;

FIG. 9 illustrates schematically the removal of a lipid bilayer using a surfactant solution;

FIG. 10 illustrates schematically a computer readable media providing a program;

FIG. 11 illustrates schematically a method of sensing an analyte; and

FIG. 12 illustrates schematically a method of recycling an analyte sensor apparatus.

DESCRIPTION OF SPECIFIC ASPECTS/EMBODIMENTS

As discussed in the background section, nanowires can be used to create highly sensitive and real-time electrically-based sensors for the detection of biological and chemical species. The underlying mechanism for nanowire sensors is a field effect that is transduced using field-effect transistors (FETs). In a standard (planar) FET, as illustrated in FIG. 1, a semiconductor such as p-type silicon 101 is supported on a substrate 102 (coated with an electrically insulating layer 110) and connected to metal source 103 and drain 104 electrodes. A current is injected and collected via the source and drain electrodes, respectively, by applying a potential difference 105 across the semiconductor. The conductance of the semiconductor between the source and drain electrodes is switched on and off by a third electrode, the gate electrode 106, capacitively coupled through a thin dielectric layer 107. Conductance may be determined by measuring the current through the semiconductor (using an ammeter 108, for example) and dividing by the potential difference. With p-type silicon (or another p-type semiconductor), application of a positive gate voltage depletes charge carriers (creating a depletion region 109 in the semiconductor) and reduces the conductance, whilst applying a negative gate voltage leads to an accumulation of charge carriers (creating a conductive channel) and an increase in conductance. The dependence of conductance on gate voltage makes FETs natural candidates for electrically-based sensing since the electric field resulting from the binding of a charged species to the gate dielectric is analogous to applying a voltage using a gate electrode.

Figure 2:
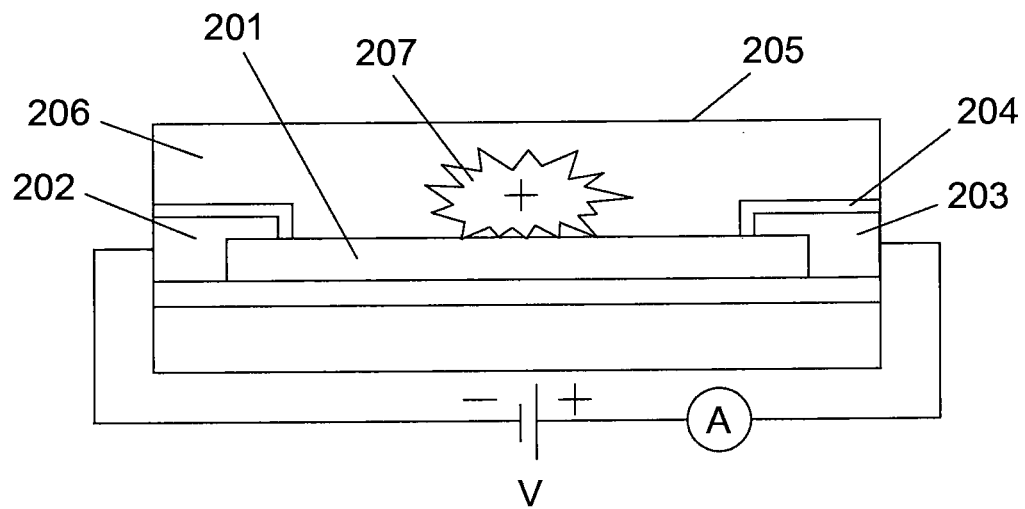

In a nanowire FET, the planar semiconductor is replaced by one or more nanowires 201 and the gate electrode is removed. A general sensing device can be configured (FIG. 2) where specific sensing is achieved by linking a recognition group to the surface of the nanowire. Silicon nanowires with their natural oxide coating make this receptor linkage straightforward, since extensive data exists for the chemical modification of silicon oxide or glass surfaces from knowledge of planar chemical and biological sensors. The sensor device illustrated further incorporates source 202 and drain 203 electrodes which are insulated from the environment by a dielectric coating 204 so that only those processes occurring at the nanowire surface contribute to the electrical signal.

The sensor device may also incorporate a microfluidic system. Microfluidics is the science of designing, manufacturing and formulating devices and processes that deal with the behaviour, precise control and manipulation of fluids that have volumes on a sub-milliliter scale (microliters, nanoliters or possibly even picoliters). The devices themselves have dimensions ranging from millimeters down to micrometers. The behaviour of fluids at this scale can differ from macrofluidic behaviour in that factors such as surface tension, energy dissipation and fluid resistance start to dominate the system.

Microfluidic systems include a number of components (such as pumps, valves, seals and channels etc) specifically adapted to control such small volumes of fluid. Microfluidic systems have diverse and widespread potential applications. In particular, microfluidic biochips utilise microfluidic systems to integrate assay operations such as detection, as well as sample pre-treatment and sample preparation on a single chip. A microfluidic channel 205 for delivery of the solutions 206 being examined can be seen in FIG. 2.

When the sensor device with surface receptor is exposed to a solution containing an analyte molecule 207 that has a net positive charge in aqueous solution, specific binding causes an increase in the surface positive charge and a decrease in conductance for a p-type nanowire device. It is of course possible to form a sensing device using an n-type nanowire instead of a p-type nanowire.

Figure 3:
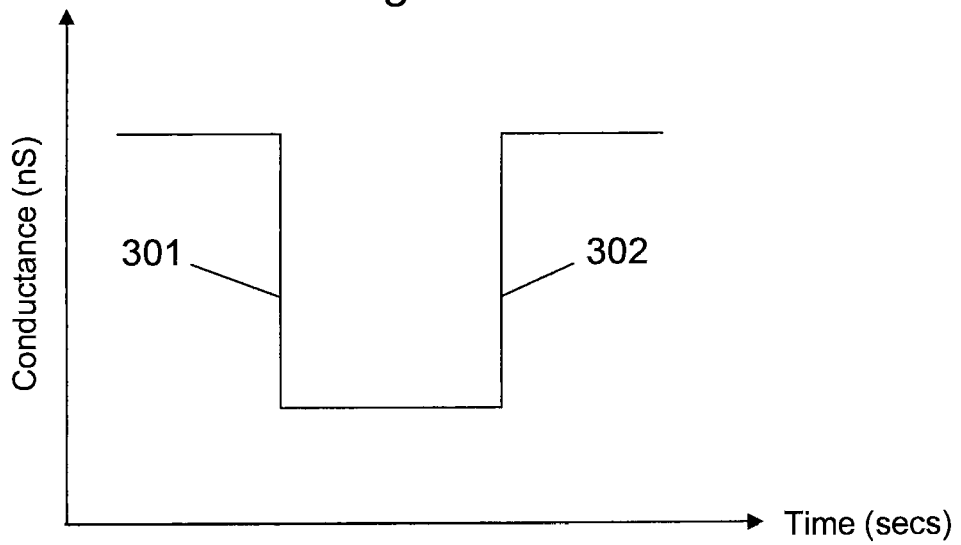
Figure 4:
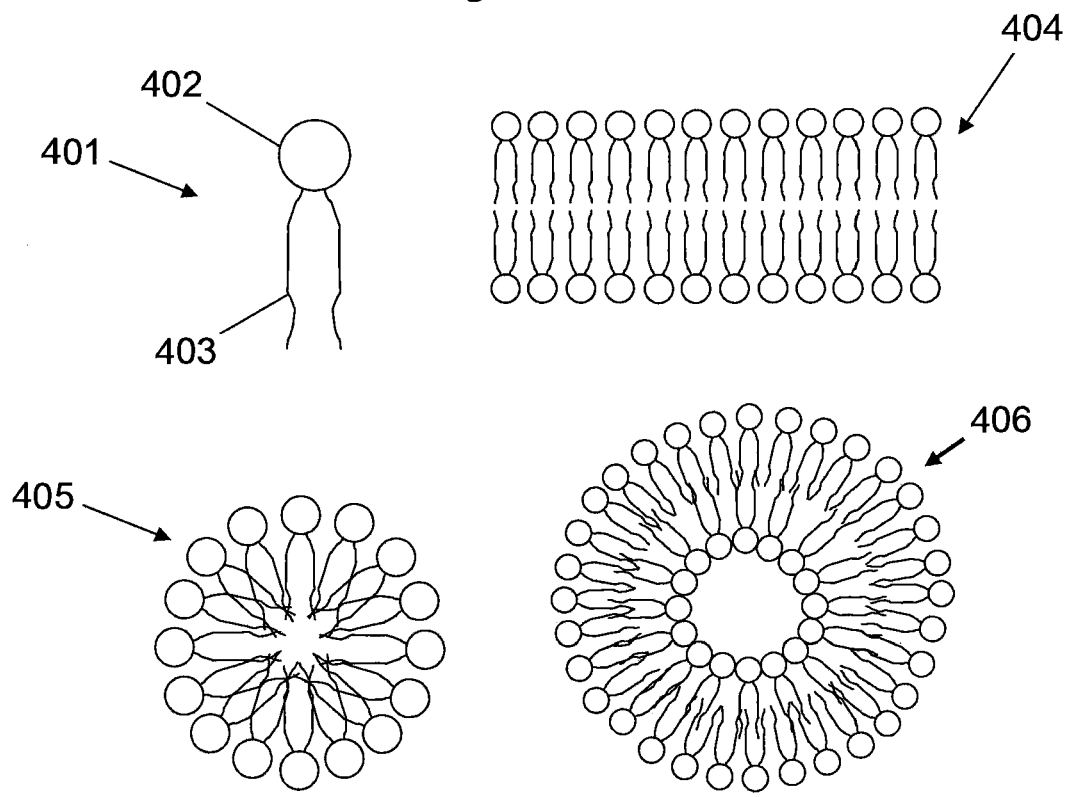

An example of a typical conductance versus time plot for a p-type nanowire sensor is given in FIG. 3, which shows a decrease in conductance 301 when an analyte molecule that has a net positive charge binds to the surface of the nanowire. Subsequent detachment of the analyte species then results in an increase in conductance 302 to the original value.

As mentioned earlier, existing nanowire FETs have shown inconsistent results, cannot be reused after the sensing event and show high specificity only when a recognition element is used in the sensing mechanism. There will now be described an apparatus and associated methods that may or may not overcome one or more of these issues.

The apparatus and methods described herein incorporate a lipid bilayer on the surface of the nanowire sensing element. A lipid bilayer is a thin membrane made up of two layers of lipid molecules 401. Lipids are small amphiphilic molecules, meaning they contain both hydrophilic 402 and hydrophobic 403 groups. The amphiphilic nature of some lipids allows them to form structures such as bilayers 404, micelles 405 and liposomes (or vesicles) 406, depending on their concentration, in an aqueous environment. Natural lipid bilayers are usually made mostly of phospholipids, which have a hydrophilic head and two hydrophobic tails. Phospholipids are similar to lipids except that they may have one or more phosphate groups covalently bonded to the hydrophilic head. Lipids self-assemble into these structures because of the hydrophobic effect, which creates an energetically unfavourable interaction between the hydrophobic tails and the surrounding water. Therefore, a lipid bilayer is held together by non-covalent forces that do not involve the formation of chemical bonds between individual molecules.

In nature, lipid bilayers form a continuous barrier around biological cells. The cell membrane of almost all living organisms and many viruses are made of a lipid bilayer, as are the membranes surrounding the cell nucleus and other subcellular structures. The cell membrane is the barrier that keeps ions, proteins and other molecules where they are needed and prevents them from diffusing into areas where they should not be. Lipid bilayers are ideally suited to this role because, even though they are only a few nanometers thick, they are impermeable to most water-soluble molecules. Bilayers are particularly impermeable to ions, which allow cells to regulate salt concentrations and pH.

Figure 5:
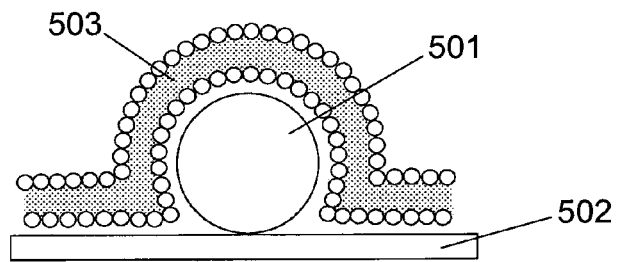

FIG. 5 shows a cross-sectional view of a nanowire sensing element 501 supported on a substrate 502 and coated with a lipid bilayer membrane 503. The lipid bilayer may be formed on the nanowire surface by spontaneous fusion of liposomes. The sensing mechanism of the present apparatus and methods, which will now be described in detail, involves opsonisation and consequent breach of the lipid bilayer membrane through activation of the complement cascade via the classical pathway.

The complement system, which forms part of the human immune system, is a biochemical cascade that helps clear pathogens from an organism. The term "complement" refers to the fact that this system complements the action of antibodies. The complement system consists of over 20 special complement (C) glycoproteins found in the blood, which normally circulate as inactive precursors. When stimulated by one of several triggers, the complement proteins interact with one another in chain reactions, or cascades. The end result of this cascade is massive amplification of the response and activation of a cell-killing membrane-attack complex. The membrane-attack complex embeds itself in the target cell forming a transmembrane channel (or pore). Formation of this pore allows free diffusion of molecules into and out of the cell. If enough pores are formed, the target cell is no longer able to survive.

The activation of complement can occur via three main routes: the classical pathway, which requires the binding of a specific antigen to an antibody receptor, the alternative pathway, which does not require antibody participation, and the lectin pathway. The present apparatus and methods advantageously use the antibody-antigen specificity of the classical pathway to detect specific analyte molecules.

Figure 6:
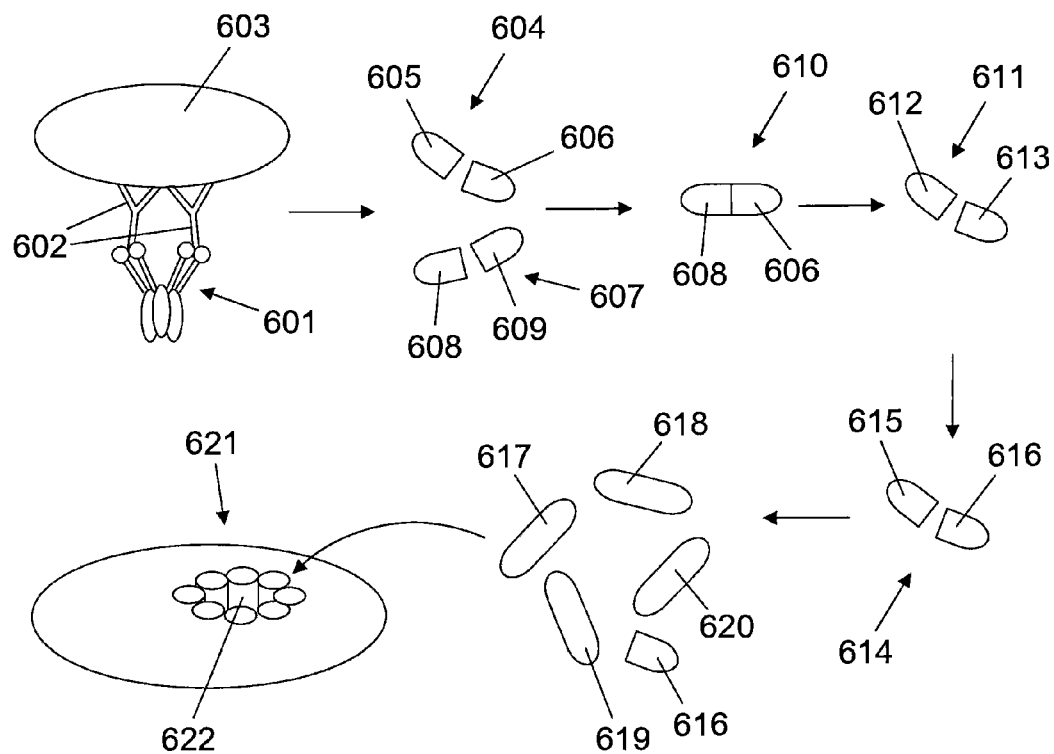

With reference to FIG. 6, the classical pathway is triggered by activation of the C1 protein 601, which occurs when C1 attaches itself to an antibody 602 already bound to a pathogen 603. Activation of the C1 protein causes cleavage of C4 (604) into C4a (605) and C4b (606), and then C2 (607) into C2a (608) and C2b (609). Protein fragments C4b and C2a subsequently bind to form the protease molecule C3 convertase 610. A protease is an enzyme that breaks down proteins by hydrolysis of the peptide bonds which link amino acids together in the polypeptide chain. C3 convertase specifically catalyses cleavage of C3 (611) to its active fragments C3a (612) and C3b (613). C3b later joins with C3 convertase to make C5 convertase which cleaves C5 (614) to C5a (615) and C5b (616). C5b initiates the membrane attack pathway, and combines with C6 (617), C7 (618), C8 (619) and polymeric C9 (620) to form the membrane-attack complex 621. As mentioned above, the membrane-attack complex then embeds itself in the pathogen creating a pore 622 in the membrane.

Given that the membrane-attack complex attacks the membranes of foreign bodies, production of the membrane-attack complex may be used to create pores in the nanowire membrane on binding of an analyte molecule to a receptor species. In effect, this could serve as a specific and indirect sensing mechanism to detect the presence of an analyte in solution. Implementation of this method is illustrated in FIG. 7.

First, the sensing surface is exposed to liposomes 701 of phospholipid molecules. The hydrophilic surface such as the silica coating 702 of a silicon nanowire or similar sensing element 703 facilitates spontaneous fusion 704 of the liposomes on the surface to create a conformal lipid bilayer 705. When the membrane-coated sensor is immersed in an ionic solution 706 (for instance an aqueous buffer solution), the lipid bilayer prevents charged species from contacting the nanowire (sensor) surface. Therefore, the lipid bilayer can be used to maintain an ionic gradient across the membrane. Since phospholipid membranes are impermeable to hydrogen ions (or protons, $H^+$), they are able to maintain an aqueous pH gradient across the membrane, at least for a certain period of time.

Figure 11:
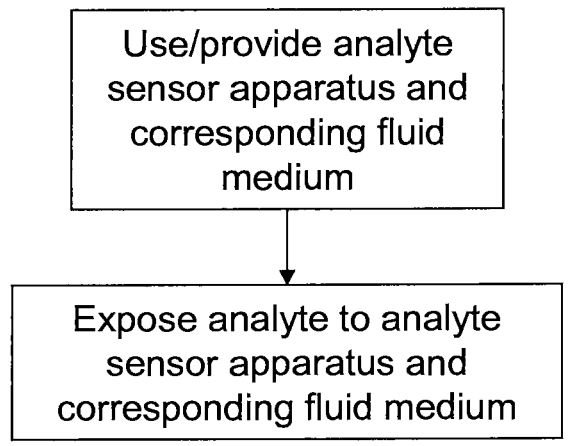

When the ionic solution further comprises a receptor species 707 and the complement proteins 711 discussed earlier, exposure of the solution to an analyte 708 results in specific analyte-receptor binding and activation of the complement system by the classical pathway. Formation of the membrane-attack complex, which subsequently embeds itself in the membrane, causes the creation of pores 709 in the membrane, allowing ions 710 in the solution to cross through the membrane and interact with the nanowire surface. The diffusion of ions through the membrane is driven by the ionic gradient. Changes in conductivity caused by the presence of charged species at the surface of the nanowire can then be detected. The aqueous buffer solution 706 may be any buffer solution which allows unambiguous detection of the charged species by the exposed nanowire sensing element. The aqueous buffer solution 706 may comprise one or more of (but not be limited to) the following: sodium ions, magnesium ions and protons. Given that activation of the complement system only occurs when a specific analyte binds to the receptor species, the detected change in conductance is indicative of the presence of that particular analyte. Furthermore, since the porosity of the membrane is proportional to the amount of analyte present in the sample, the conductance of the nanowire also provides quantitative information. This method (the key steps of which are illustrated schematically in FIG. 11) therefore provides a highly selective sensing mechanism without the need to bind the analyte or receptor species directly to the surface of the nanowire.

Figure 7:
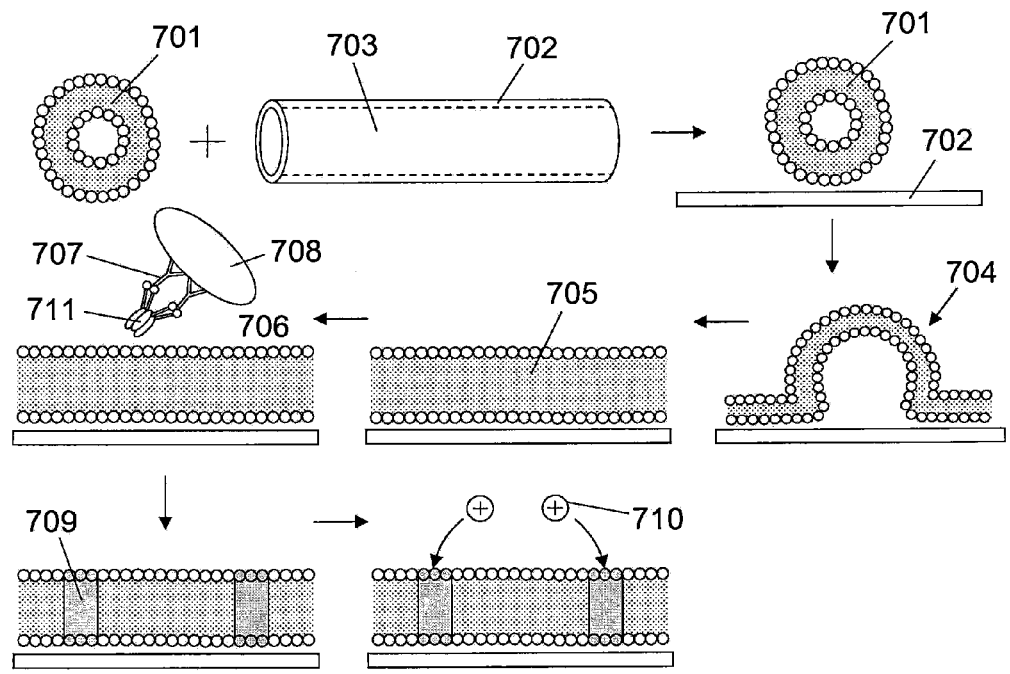
Figure 8:
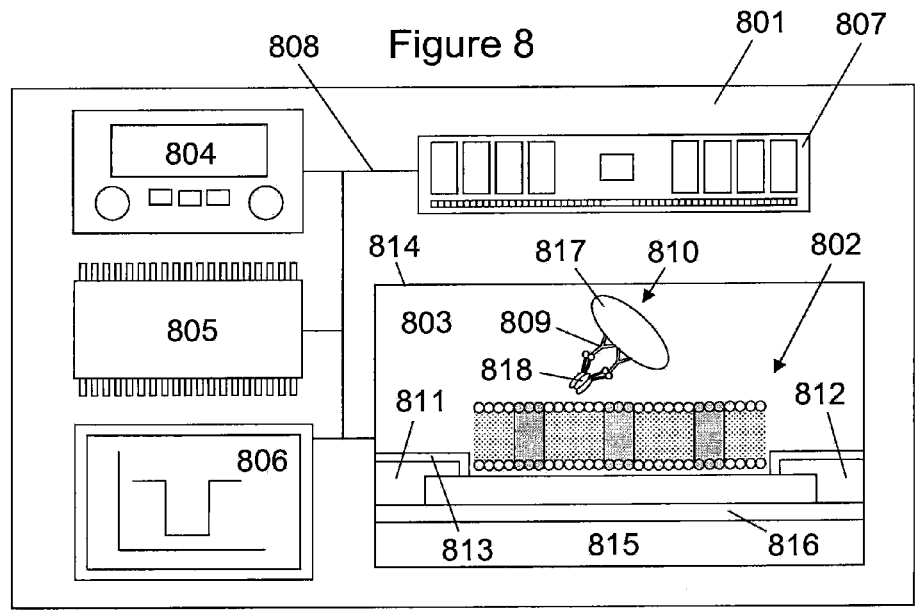

FIG. 8 illustrates schematically a sensor device 801 comprising the membrane-coated nanowire 802 and solution 803 as described with respect to FIG. 7. The device further comprises a measurement apparatus 804, a processor 805, a display apparatus 806 and a storage medium 807, which may be (removably) electrically connected to one another by a data bus 808. The solution, herein referred to as the corresponding fluid medium comprises the receptor species 809, the complement proteins 818 (or perhaps some other activatable species capable of creating pores in the membrane when activated by a specific analyte-receptor binding event 810) and a charged species. The sensor device further comprises source 811 and drain 812 electrodes which are insulated from the environment by a dielectric coating 813, a microfluidic channel 814 to contain the corresponding fluid medium and sample being examined, and a microfluidic device (not shown) for delivery of these fluids. Microfluidics is the science of designing, manufacturing and formulating devices and processes that deal with the behaviour, precise control and manipulation of fluids that have volumes on a sub-milliliter scale (microliters, nanoliters or possibly even picoliters). Microfluidic devices themselves have dimensions ranging from millimeters down to micrometers. The behaviour of fluids at this scale can differ from macrofluidic behaviour in that factors such as surface tension, energy dissipation and fluid resistance start to dominate the system. Microfluidic systems include a number of components (such as pumps, valves, seals and channels etc) specifically adapted to control such small volumes of fluid. Microfluidic systems have diverse and widespread potential applications. In particular, microfluidic biochips utilise microfluidic systems to integrate assay operations (such as detection, sample pre-treatment and sample preparation) on a single chip.

The nanowire is supported on a substrate 815 which is coated with an electrically insulating layer 816 to isolate the electrical contacts from the supporting substrate. The nanowire may be formed using the vapour-liquid-solid (VLS) mechanism or catalytic chemical vapour deposition (CVD) procedures, and deposited on the surface of the supporting substrate using a flow-alignment procedure. The electrical contacts may then be fabricated using a lithographic process.

The measurement apparatus 804 is removably connected to the source and drain electrodes by electrical connectors (although in other embodiments it may be non-releasably connected, e.g. hard-wired). The removable connections allow the nanowire to be disconnected and physically removed from the other device components for modification or replacement. The measurement apparatus is used to apply a potential difference across the nanowire, measure the current through the nanowire, and determine the conductance or other electrical property of the nanowire. The processor 805 receives the electrical data and processes the data for display on the display apparatus 806. This allows the electrical response of the nanowire to be observed visually. The processor 805 may also process the electrical data to determine the presence and quantity of the analyte species 817. The processor 805 may determine the presence and quantity of the analyte species 817 by comparing the received data with data previously stored in a database to determine a match. On the other hand, the processor 805 may simply pass the processed data to the display apparatus 806 for manual analysis. The storage medium 807 is used to store the electrical data, and may also be used to store the database. The storage medium 807 may be a temporary storage medium such as a volatile random access memory, or may be a permanent storage medium such as a hard disk drive, flash memory or non-volatile random access memory.

If the measurement device 804 is removably coupled (although not just limited to this circumstance), it is possible to supply a kit comprising the analyte sensor (e.g. the membrane-coated nanowire 802) together with a corresponding fluid medium 803 (e.g. comprising one or more of a receptor species 809, an activatable species 818 and a charged species in various combinations) to sense a particular analyte 817. The receptor species 809 may comprise one or more affinity agents (such as an antibody). The activatable species 818 may comprise one or more complement proteins (e.g. C1), or possibly the complete group of complement proteins (C-proteins and protein fragments). The analyte 817 may comprise one or more pathogens (e.g. viral, bacterial, fungal, eukaryotic or prionic pathogens). The charged species may comprise one or more charged atomic (e.g. hydrogen ions), molecular (e.g. proteins) or subatomic species (e.g. protons or electrons). It may be useful to supply a control amount of the analyte 817 so that one can confirm that the sensor is capable of detecting the analyte 817. Furthermore, the corresponding fluid medium 803 could be supplied separately from the analyte sensor 802 and measurement device 804.

The sensor device 801 may comprise either individual sensing elements 802 (e.g. nanowires) or arrays of sensing elements connected together in an electrical circuit. Each sensing element may be individually addressable both electronically, and in terms of liquid sample exchange via the microfluidic system. There are two formats of sensing element: one where multiple nanowires are covered with a single membrane, and another where a single nanowire is covered with a single membrane. In the former case, the nanowires may be individually addressed in the electronic circuit with the circuits operated in parallel, or multiple nanowires may be deposited between source 811 and drain 812 electrodes so that current is able to flow from one nanowire to the next.

In these examples, one or more nanowires are connected to a pair of metallic source 811 and drain 812 electrodes. The nanowires may be made from a uniform material for quality and performance. Typically the nanowires are crystalline with a thin layer of native oxide on the surface. The nanowire FETs can be fabricated by depositing the nanowires on either a hydrophilic or hydrophobic surface, and connecting the deposited nanowires to the source 812 and drain 813 electrodes using conventional photolithography. Passivation of the electrodes (obtained by coating them with an electrical insulator 813) is a critical step for these devices as they will operate in aqueous solution. The membrane coating may be continuous (i.e. covering the nanowires and supporting substrate 815) if the substrate is hydrophilic, or discontinuous (i.e. coating the nanowires but not the supporting substrate 815) if the substrate is hydrophobic. A reference gate electrode may be added to the sensing element (as per a standard planar FET).

The electronic circuit of sensing elements may be incorporated with the microfluidic system so that liquid can only follow prescribed routes to and from the sensing elements. The microfluidic system may comprise sample inlets, solution reservoirs, microchannels, waste reservoirs and, if required, pumping mechanisms. The exact architecture will vary depending on the particular species involved, and whether single sensing elements or arrays of sensing elements are employed. Each sensing element could have the option of being individually addressable and hence being operated in isolation from any other sensing elements in terms of both the microfluidics and the electronic control mechanisms.

The sensing element may be connected to a microchannel 814 comprising an inlet and an outlet for delivering solutions. To simplify waste removal, the solution in the microchannel 814 may be configured to flow in one direction from the inlet to the outlet. The solution reservoirs will typically contain (but are not be limited to) sample dilution buffer, a supply of lipids to generate the membrane, a supply of surfactant for membrane removal (see later), solutions of reagents (for instance the receptor 809 and the complement proteins 818), and reaction buffers at different pHs for the correct functioning of the sensing mechanism.

The sensing mechanism requires a highly specific binding event between the target analyte and the receptor 809. In the present case, the receptor needs to have two functions, it must specifically recognize and bind the target analyte, and, only when bound to the analyte, it must interact with the complement proteins 818 to initiate the complement cascade leading to increasing the porosity of the membrane coating the sensing element.

Receptors fulfilling these requirements include mammalian antibodies. There has been extensive research into the nature and identity of the analytes that can be recognized by mammalian antibodies. In general the targets must be above a certain size in order to form a sufficient number of chemical interactions with the analyte binding site of the antibody so that specificity and avidity are achieved. Hence antibodies are highly unlikely to recognize monoatomic ions such as hydrogen ions or metal ions. However, antibodies will recognize and bind larger molecules, and will bind polymers where multiple potential binding sites are presented. There are known examples of both inorganic and organic molecules which are recognized by antibodies.

Antibodies are frequently used as the affinity reagent in biosensors. The commonest isotype used is the immunoglobulin G (IgG) molecule, and though this sensing mechanism would work with the other subtypes as long as they can activate complement, it is most likely that most applications will use IgG as the majority of commercially available antibodies with defined target specificities are IgG molecules. Monoclonal antibodies with well-defined binding targets are typically IgG.

Antibodies are made of one or more protein chains. Each mammalian antibody contains two identical large "heavy" chains, and two identical copies of a "light chain". Though the general structure of all antibodies is very similar, a small region at the tip of the protein (the paratope) is extremely variable, allowing millions of antibodies with slightly different tip structures, or antigen binding sites, to exist. This region is known as the hypervariable region. Each of these variants can bind to a different target (antigen). This huge diversity of antibodies allows the immune system to recognize an equally wide diversity of antigens. Engineered antibody fragments can be also considered for the sensing mechanism, but for this application the fragment would have to be able to bind and activate the complement cascade, and most common types of antibody fragments have lost this function.

The unique part of the antigen (analyte) recognized by an antibody is called an epitope. Epitopes bind with their antibody in a highly specific interaction, called induced fit, which allows antibodies to identify and bind only their unique antigen in the midst of the millions of different molecules that make up an organism. Hydrogen bonds, hydrophobic bonds, electrostatic forces, and van der Waals forces influence the binding between antigens and antibodies. Moreover, pH, temperature and solvent play an important role in the stability of the complex. These are all bonds of a weak, non-covalent nature, yet some associations between an antigen and an antibody can be quite strong. Accordingly, the affinity constant for antibody-antigen binding can span a wide range, extending from below $10^5$ mol$^{-1}$ to more than $10^{12}$ mol$^{-1}$. Apart from the affinity of an antibody for an antigen, the overall stability of an antibody-antigen complex is also determined by the valency of the antigen and antibody and the structural arrangement of their interacting parts (epitope and paratope).

Accurate affinity constants can only be determined for monoclonal antibodies. Monoclonal antibodies are genetically identical molecules recognising one single epitope on the antigen. With polyclonal antibodies, on the other hand, a broad distribution of affinities may contribute to an apparent affinity constant. The apparent affinity constant may also be caused by the fact that polyclonal antibodies can recognise more than one epitope on the same antigen. Since antibodies normally harbor more than one binding domain per molecule, multiple co-operative bindings can take place between polyclonal antibodies and their antigens. This effect is termed avidity. As monoclonal antibodies react with only one single epitope on the antigen, they are more vulnerable to the loss of epitope through chemical treatment of the antigen than polyclonal antibodies. This can be offset by pooling two or more monoclonal antibodies to the same antigen.

Sensor devices that incorporate lipid membranes can be expensive to fabricate in cost and time. Therefore, the ability to use the same nanowire more than once would be advantageous. Unfortunately, however, lipid membranes cannot be reused after the sensing event, either because of pore damage to the membrane, or because molecular species are embedded in the membrane (as described in the background section). In the latter case, interactions between the new sensor species and pre-existing sensor species can occur, these interactions affecting operation and sensitivity of the device. There will now be described a method of recycling an analyte sensor apparatus using a surfactant that may overcome this issue.

Surfactants (surface active agents), like lipids, are amphiphilic molecules, i.e. one end of the surfactant molecule (the head) is hydrophilic and the other end is hydrophobic (the tail). The hydrophobic end is also referred to as being lipophilic, meaning that it is attracted to fat molecules. If a solution of surfactant and water is added to fat, the lipophilic ends of the surfactant molecules bind to fat molecules and the hydrophilic ends bind to nearby water molecules. In this way, the fat becomes suspended in the water, a process known as emulsification. The dual nature of surfactant molecules reduces the interfacial tension between the fat and water, thereby boosting the "wetting" ability of the water. This feature makes surfactants effective cleaners, because they can emulsify the oil and grease that holds dirt in place.

As a result of their amphiphilic nature, surfactants locate at the phase boundary between oil and water until the phase boundary becomes saturated. Beyond the point of saturation, the surfactant molecules congregate together and form micelles. The concentration at which surfactants begin to form micelles is known as the critical micellar concentration (CMC). When micelles form in water, their lipophilic tails form a core that can encapsulate an oil droplet, and their hydrophilic heads form an outer shell that maintains favourable contact with the water. On the other hand, when surfactants assemble in oil, the aggregate is referred to as a reverse micelle. In a reverse micelle, the hydrophilic heads form a core and their lipophilic tails maintain favourable contact with the oil. The thermodynamics of surfactant systems are important both theoretically and practically, because they represent systems between ordered and disordered states of matter. Surfactant solutions may contain both an ordered phase (micelles) and a disordered phase (free surfactant molecules).

Figure 9:
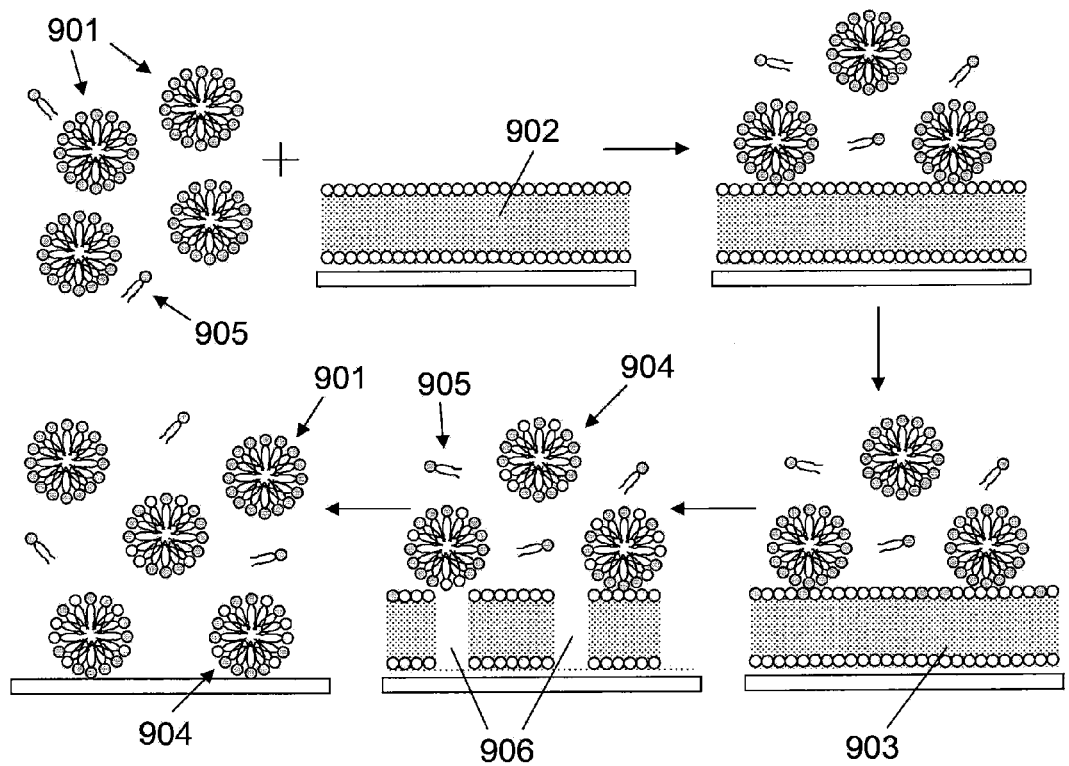

Regarding the recycling of an analyte sensor apparatus, surfactants interact with lipid bilayer membranes to form mixed micelles. This process is known as "solubilisation of the double layer" and comprises various stages, as illustrated in FIG. 9. First, surfactant molecules 905 are introduced at or above the CMC to form surfactant micelles 901. The surfactant molecules then intercalate into the lipid bilayer 902 creating mixed lipid-surfactant bilayers 903, mixed lipid-surfactant micelles 904 and free surfactant molecules (monomers) 905. This process breaks down the integrity of the lipid bilayer (shown as holes 906 in the membrane). As intercalation progresses, mixed lipid-surfactant bilayers coexist with mixed lipid-surfactant micelles until complete disruption of the membrane occurs. At this stage, mixed micelles are in equilibrium with surfactant micelles and free surfactant molecules.

Figure 12:
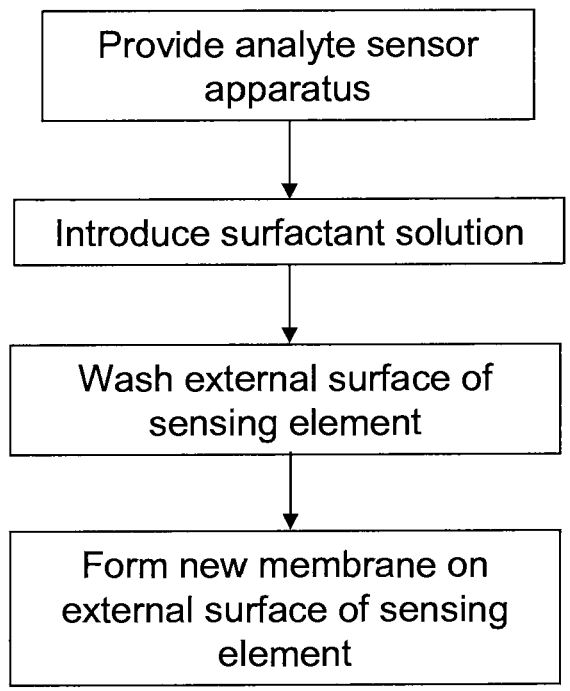

The ability to form (spontaneous fusion) and dissolve (solubilisation) membranes should allow membrane coatings to be made and removed in-situ within a sensor device. Therefore, it should be possible, post sensing event, to dissolve the porous or embedded membrane and form a new membrane coating so that the sensor device may be reused. This procedure, the key steps of which are illustrated schematically in FIG. 12, saves both time and money spent on fabrication. For clarity, the fusion-sensing-solubilisation cycle is as follows:

Liposomes of lipid are first introduced at the surface of the sensing element and spontaneously fuse to create a lipid bilayer. The surface is then washed to remove any excess lipid molecules. Following this, the membrane-coated sensing element is exposed to the various components of the sensing reaction to detect the presence of the analyte (as described with reference to FIG. 7, for example). The sensing procedure causes damage to the membrane by creating pores or embedding molecular species in the membrane to generate a signal. The components of the sensing reaction are then removed from the system (washed away) and a surfactant solution is introduced. The concentration of surfactant may or may not be sufficient to form surfactant micelles, although solubilisation occurs faster and is more efficient when the concentration of surfactant is greater than or equal to the CMC. The surfactant breaks down the integrity of the membrane (or remaining damaged membrane) until complete disruption of the membrane is achieved together with the formation of lipid-surfactant micelles. The sensing element is then washed to leave a clean surface, before micelles or liposomes of lipid are reintroduced to form a new lipid bilayer. The new bilayer is intact and ready for the next sensing event.

A practical example of how to operate the device will now be described. It should be noted, however, that there are several different ways of constructing and using the sensing device, and the following example is just one of these possibilities. This description is divided into four sections, namely (i) preparation of the liposomes, (ii) deposition of the liposomes to form a membrane, (iii) incubation of target analyte with antibody and complement, and (iv) removal of the damaged bilayer.

(i) Preparation of the Liposomes

The lipid used to prepare small unilamellar liposomes could be (but is not limited to) dioleoyl phosphatidylcholine (DOPC). The requirement is that the lipid is neutral otherwise a charged lipid (either positive or negative) could lead to the inappropriate activation of the complement system without the specific antigen-antibody recognition. In some cases the process might be followed optically, in which case the DOPC will be doped with a small amount (typically 2%) of a fluorescent lipid probe such as NBD-PE (1,2-dioleoyl-sn-glycero-3-phosphoethanolamine-N-(7-nitro-2-1,3-benzoxadiazol-4-yl)). The following is an established method. Briefly, a chloroform solution of each lipid species is prepared. A desired amount of the lipids is mixed with a fluorescence lipid in a flask. The organic solvent is evaporated by nitrogen and the dried lipid film is re-suspended by vigorous mixing in the desired buffer solution. The lipid suspension is then extruded 11 times through two 200 nm nucleopore polycarbonate membranes using a commercial available lipid extruder (for instance the Mini-extruder from Avanti Lipids).

(ii) Deposition of the Liposomes to Form a Membrane

There are two possible mechanisms: the first mechanism (a) involves forming the membrane and adding the antibody, analyte and complement later, whilst the second mechanism (b) involves pre-incubating the antibody with the lipid vesicles before membrane deposition. The latter relies on non-specific interaction between the lipids and the proteins to drive the association of the antibody with the membrane. Further testing is required to determine the best method, and it is likely that the choice of method will depend on the identity of the analyte and the antibody. Both methods are presented below:

a) Membrane Formation

Fusion of Pure Small Lamellar Liposomes on $SiO_2$ Nanowires

The liposome suspension is injected directly into the measuring chamber where one or more nanowires are present. The mixture is left to equilibrate for 30 min. The spontaneous fusion of liposomes on the hydrophilic surface of the nanowires is a diffusion limited process. After sufficient incubation to create a continuous layer of lipid, the device is washed with buffer in order to remove the unbound liposomes.

Interaction Between Planar Membrane and Antibody Suspension

Add the appropriate amount of antiserum to the buffer suspension and mix well. Add the solution into the sensing element chamber and incubate for 15 min at 37° C. After the incubation, wash the sensing element three times with buffer by in order to remove any unbound antibody. The conductance of the nanowire FET is then measured to confirm that the membrane formed is impermeable to ions.

b) Membrane-Antibody Complex Formation

Preparation of Standard Liposomes-Antibody Complex Suspension

Add the appropriate amount of antiserum (antibody solution) to the buffer suspension and mix well. Pour the liposome solution into the antibody-buffer mixtures and mix well. The suspension of the liposomes is mixed slowly with an equal volume of antiserum with constant stirring. Exact concentrations of lipids, antibodies and buffer volumes will be determined empirically. The suspension is transferred in a bath of 37° C. and incubated for 15 min with constant shaking. After incubation, the liposomes are concentrated by centrifugation and then washed three times with buffer by centrifugation for 15 min at 8500 rpm to remove unincorporated antibody.

Fusion of Small Lamellar Liposomes-Antibody on $SiO_2$ Nanowires

The liposomes-antibody solution is injected directly into the measuring chamber where one or more nanowires are present. The solution is left to equilibrate for 30 min. The spontaneous fusion of liposomes-antibody on the hydrophilic surface of the nanowires is a diffusion limited process. After sufficient incubation to create a continuous layer of lipid, the device is washed with buffer in order to remove the unbound liposomes. The conductance of the nanowire FET is then measured to confirm that the membrane formed is impermeable to ions.

(iii) Incubation of Target Analyte with Antibody and Complement

Antigen and a solution of complement proteins are added to the chamber and incubated at 37°. The time required for the antigen to bind an antibody and activate the complement cascade needs to be determined whenever a new type of antibody, antigen and complement is used. During this time the pH of the solution around the nanowire FET is monitored by measuring the conductance. If the antigen is present, pores are formed and diffusion of ions across the membrane occurs, as detected by a change in the conductance of the nanowire. Complement lysis is often determined as the ability of a volume of serum to lyse 50% of $5*10^8$ cells. This volume is defined as $CH_{50}$.

Establishing the normal serum $CH_{50}$ range needs to be done each time a new antibody is tested. This may be performed away from the sensor device during preparation.

(iv) Removal of the Damaged Bilayer

The surfactant used may be LDAO (Lauryldimethylamine-oxide), although the surfactant chosen depends on the lipid used to create the membrane. The solubilization process is strongly coupled with the surfactant and the lipid concentration. The solubilization concentration ($c_s$) for the surfactant depends on the lipid concentration on the bilayer. A surfactant solution at concentration $c > c_s$ is injected into the measuring chamber where the nanowires coated with the now-porous lipid membrane are present. The surfactant solution is left to equilibrate for one hour. After the surfactant has removed the lipid layer on the nanowires (creating mix-micelles), buffer solution is injected in order to wash the measuring chamber. Conductance measurements are used to ensure that any ion-impermeable barrier has been removed from the chamber.

Protocols developed to exploit complement activity very often use buffers with a complex mixture of components in order to maintain the activity of the different components of the complement cascade. The choice of buffer depends essentially on the complement, antigen and antibody used.

Figure 10:
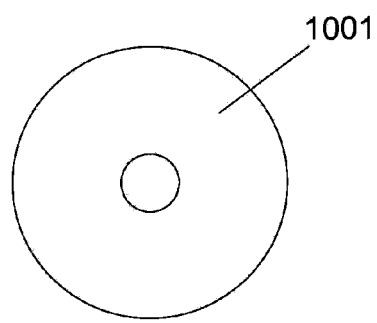

Suitable buffers may include:

Mancini Modified Buffer:
100 ml 0.3 M $K_2HPO_4$;
<7 ml 0.3 M $KH_2PO_4$ until pH is 8.0±0.05;
Place 100 ml of this mixture in a 1-liter volumetric flask and add:
5.84 g NaCl (0.15 M);
100 ml of 0.1 M EDTA (3.58 g salt);
30.0 g polyethylene glycol (PEG) 6000;
1.0 ml Tween-20;
2.0 ml 10% (w/v) $NaN_3$;
1 liter of DI water TA-CHB (TriethanolAmine-Complement Hemolysis Buffer) Buffer:
prepare solution A: 42.66 g NaCl (0.73 M) and 4.134 g TA.HCl in 900 ml of DI water;
prepare solution B: 1.0 M $MgCl_2$ and 0.3 M $CaCl_2$;
add 2.5 ml of solution B to solution A;
bring the buffer to a final volume of 1.0 liter in DI water FIG. 10 illustrates schematically a computer/processor readable media 1001 providing a computer program according to one embodiment. The computer program may comprise code for sensing the presence of an analyte. In this example, the computer/processor readable media is a disc such as a digital versatile disc (DVD) or a compact disc (CD). In other embodiments, the computer readable media may be any media that has been programmed in such a way as to carry out an inventive function. The readable media may be a removable memory device such as a memory stick or memory card (SD, mini SD or micro SD).

The computer program may comprise code to detect an electrical signal produced from an analyte sensor apparatus and a corresponding fluid medium, the analyte sensor apparatus comprising a nanowire, the external surface of which is coated by a membrane to inhibit exposure of the nanowire, the corresponding fluid medium comprising a receptor species and an activatable species, the receptor species for binding to an analyte to activate the activatable species, activation of the activated species causing increased porosity of the membrane of an in-contact analyte sensor apparatus to correspondingly increase exposure of the nanowire to allow for production of a detectable electrical signal which can be used to sense the presence of the analyte.

The applicant hereby discloses in isolation each individual feature described herein and any combination of two or more such features, to the extent that such features or combinations are capable of being carried out based on the present specification as a whole, in the light of the common general knowledge of a person skilled in the art, irrespective of whether such features or combinations of features solve any problems disclosed herein, and without limitation to the scope of the claims. The applicant indicates that the disclosed aspects/embodiments may consist of any such individual feature or combination of features. In view of the foregoing description it will be evident to a person skilled in the art that various modifications may be made within the scope of the disclosure.

While there have been shown and described and pointed out fundamental novel features as applied to different embodiments thereof, it will be understood that various omissions and substitutions and changes in the form and details of the devices and methods described may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment may be incorporated in any other disclosed or described or suggested form or embodiment as a general matter of design choice. Furthermore, in the claims means-plus-function clauses are intended to cover the structures described herein as performing the recited function and not only structural equivalents, but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

The invention claimed is:

1. An analyte sensor apparatus and a corresponding fluid medium,
the analyte sensor apparatus comprising a sensing element, the external surface of which comprises a membrane to inhibit exposure of the sensing element;
the corresponding fluid medium comprising a receptor species and an activatable species, the receptor species for interacting with an analyte to activate the activatable species, activation of the activated species causing increased porosity of the membrane of an in-contact analyte sensor apparatus to correspondingly increase exposure of the sensing element to allow for production of a detectable electrical signal which can be used to sense the presence of the analyte;
wherein the receptor species comprises an antibody; and
wherein the analyte sensor apparatus comprises part of a nanowire field effect transistor.

2. The analyte sensor apparatus and fluid medium of claim 1, wherein the analyte sensor apparatus is configured such that the analyte itself, in-contact with the membrane, does not cause increased porosity of the membrane.

3. The analyte sensor apparatus and fluid medium of claim 1, wherein the activatable species comprises complement proteins, and wherein the activatable species is configured such that activation of the activatable species by the analyte triggers a complement cascade to produce a membrane-attack complex from the complement proteins which causes increased porosity of the membrane.

4. The analyte, sensor apparatus and fluid medium of claim 1, wherein the fluid medium comprises a charged species configured to provide an ionic gradient across the membrane.

5. The analyte sensor apparatus and fluid medium of claim 1, wherein the fluid medium comprises a charged species configured to produce a detectable electrical signal when in-contact with the sensing element.

6. The analyte sensor apparatus and fluid medium of claim 1, wherein the membrane is configured to be impervious to a charged species comprised in the fluid medium, the charged species configured to provide an ionic gradient across the membrane, and wherein the increased porosity of the membrane caused by activation of the activatable species allows the charged species to diffuse through the created pores in the membrane from the corresponding fluid medium to cause a change in charge concentration at the exposed surface of the sensing element.

7. The analyte sensor apparatus and fluid medium of claim 6, wherein the charged species comprises protons such that diffusion of the protons through the membrane from the corresponding fluid medium causes a change in pH or a change of surface density charge at the external surface of the sensing element.

8. The analyte sensor apparatus and fluid medium of claim 1, wherein the analyte sensor apparatus further comprises source and drain electrodes, the source and drain electrodes electrically connected to the sensing element such that an electrical current may flow from the source electrode through the sensing element to the drain electrode when a potential difference is applied across the source and drain electrodes.

9. The analyte sensor apparatus and fluid medium of claim 8, wherein the analyte sensor apparatus is configured such that electrical connectors are electrically connected to the source and drain electrodes to apply the potential difference.

10. The analyte sensor apparatus and fluid medium of claim 9, wherein the analyte sensor apparatus is configured such that the electrical connectors are removably connected to the source and drain electrodes.

11. The analyte sensor apparatus and fluid medium of claim 8, wherein the analyte sensor apparatus is configured such that the source and drain electrodes are electrically insulated from the corresponding fluid medium.

12. The analyte sensor apparatus and fluid medium of claim 8, wherein the analyte sensor apparatus is configured such that the conductance of the sensing element varies with charge concentration at the external surface of the sensing element.

13. The analyte sensor apparatus and fluid medium of claim 1, wherein the receptor species is capable of specifically interacting with the analyte.

14. A fluid medium for use with a corresponding analyte sensor apparatus comprising a sensing element, the external surface of which comprises a membrane to inhibit exposure of the sensing element; the fluid medium comprising a receptor species and an activatable species, the receptor species for interacting with an analyte to activate the activatable species, activation of the activated species causing increased porosity of the membrane of an in-contact analyte sensor apparatus to correspondingly increase exposure of the sensing element to allow for production of a detectable electrical signal which can be used to sense the presence of the analyte;
    wherein the receptor species comprises an antibody; and
    wherein the analyte sensor apparatus comprises part of a nanowire field effect transistor.

15. A method of sensing an analyte, the method comprising: using/providing an analyte sensor apparatus and a corresponding fluid medium, the analyte sensor apparatus comprising a sensing element, the external surface of which comprises a membrane to inhibit exposure of the sensing element, the corresponding fluid medium comprising a receptor species and an activatable species, the receptor species for interacting with an analyte to activate the activatable species, activation of the activated species causing increased porosity of the membrane of an in-contact analyte sensor apparatus to correspondingly increase exposure of the sensing element to allow for production of a detectable electrical signal which can be used to sense the presence of the analyte; and exposing the analyte to the corresponding fluid medium and analyte sensor apparatus to allow for production of a detectable electrical signal which can be used to sense the presence of the analyte;
    wherein the receptor species comprises an antibody; and
    wherein the analyte sensor apparatus comprises part of a nanowire field effect transistor.

16. A non-transitory computer readable storage medium tangibly embodying a computer program of executable instructions for sensing the presence of an analyte, the computer program comprising computer code to detect an electrical signal produced from an analyte sensor apparatus and a corresponding fluid medium, the analyte sensor apparatus comprising a sensing element, the external surface of which comprises a membrane to inhibit exposure of the sensing element, the corresponding fluid medium comprising a receptor species and an activatable species, the receptor species for interacting with an analyte to activate the activatable species, activation of the activated species causing increased porosity of the membrane of an in-contact analyte sensor apparatus to correspondingly increase exposure of the sensing element to allow for production of a detectable electrical signal which can be used to sense the presence of the analyte;
    wherein the receptor species comprises an antibody; and
    wherein the analyte sensor apparatus comprises part of a nanowire field effect transistor.

17. A method of recycling an analyte sensor apparatus of a nanowire field effect transistor, the method comprising:
    providing an analyte sensor apparatus, the analyte sensor apparatus comprising a sensing element, the external surface of which comprises a membrane comprising a receptor species comprising an antibody;
    introducing a surfactant solution to interact with and break down the integrity of the membrane;
    washing the external surface of the sensing element; and
    forming a new membrane on the external surface of the sensing element.

18. The use of an analyte sensor apparatus, and corresponding fluid medium for detecting the presence of an analyte, the use comprising: providing an apparatus and corresponding fluid medium, the analyte sensor apparatus comprising a sensing element, the external surface of which comprises a membrane to inhibit exposure of the sensing element, the corresponding fluid medium comprising a receptor species and an activatable species, the receptor species for interacting with an analyte to activate the activatable species, activation of the activated species causing increased porosity of the membrane of an in-contact analyte sensor apparatus to correspondingly increase exposure of the sensing element to allow for production of a detectable electrical signal which can be used to sense the presence of the analyte; and instructing exposure of the analyte to the corresponding fluid medium and analyte sensor apparatus to allow for production of a detectable electrical signal which can be used to sense the presence of the analyte;
    wherein the receptor species comprises an antibody; and
    wherein the analyte sensor apparatus comprises part of a nanowire field effect transistor.

\* \* \* \* \*